(12) United States Patent  
Iwami

(10) Patent No.: US 11,594,322 B2
(45) Date of Patent: Feb. 28, 2023

(54) DISPENSING AUDIT SUPPORT APPARATUS AND DISPENSING AUDIT SUPPORT METHOD

(71) Applicant: FUJIFILM Toyama Chemical Co., Ltd., Tokyo (JP)

(72) Inventor: Kazuchika Iwami, Ashigarakami-gun (JP)

(73) Assignee: FUJIFILM TOYAMA CHEMICAL CO., LTD., Tokyo (JP)

( * ) Notice: Subject to any disclaimer, the term of this patent is extended or adjusted under 35 U.S.C. 154(b) by 450 days.

(21) Appl. No.: 16/662,233

(22) Filed: Oct. 24, 2019

(65) Prior Publication Data

US 2020/0058392 A1    Feb. 20, 2020

Related U.S. Application Data

(63) Continuation of application No. PCT/JP2018/016282, filed on Apr. 20, 2018.

(30) Foreign Application Priority Data

May 30, 2017    (JP) .............................. JP2017-106815

(51) Int. Cl.
*G16H 30/40*    (2018.01)
*G06T 7/70*    (2017.01)
(Continued)

(52) U.S. Cl.
CPC ............ *G16H 30/40* (2018.01); *G06T 7/0002* (2013.01); *G06T 7/70* (2017.01); *G16H 20/13* (2018.01);
(Continued)

(58) Field of Classification Search
CPC ........ G16H 30/20; G16H 30/40; G16H 20/10; G16H 20/13; G06T 7/62; G06T 7/70;
(Continued)

(56) References Cited

U.S. PATENT DOCUMENTS

2003/0083850 A1    5/2003 Schmidt et al.
2004/0228526 A9    11/2004 Lin et al.
(Continued)

FOREIGN PATENT DOCUMENTS

CN        104173190 A    12/2014
CN        104176334 A    12/2014
(Continued)

OTHER PUBLICATIONS

Lee et al., "Pill-ID: Matching and retrieval of drug pill images", Sep. 2011, Elsevier, Pattern Recognition Letters, vol. 33, p. 904-910. (Year: 2011).*
(Continued)

*Primary Examiner* — Vincent Rudolph
*Assistant Examiner* — Timothy Choi
(74) *Attorney, Agent, or Firm* — Birch, Stewart, Kolasch & Birch, LLP

(57) ABSTRACT

An object of the present invention is to provide a dispensing audit support apparatus and a dispensing audit support method with a high collation accuracy robustness. According to a dispensing audit support apparatus according to one aspect of the present invention, since a position, shape and size of a region of interest are set according to a position of a collation-target medicine in a captured image, and a position, shape and size of a master image are set according to the set region of interest, it is possible to avoid or reduce distortion of the medicine shape, blur, inclusion of an end part into the image, and the like due to the position and orientation of the collation-target medicine. Therefore, influence on collation accuracy is small, and it is possible to enhance the robustness of the collation accuracy.

8 Claims, 13 Drawing Sheets

(51) Int. Cl.
*G06T 7/00* (2017.01)
*G16H 30/20* (2018.01)
*G16H 20/13* (2018.01)

(52) U.S. Cl.
CPC ... *G16H 30/20* (2018.01); *G06T 2207/20212* (2013.01)

(58) Field of Classification Search
CPC ............. G06T 7/74; G06T 2207/20212; G06T 7/0002; G06T 7/0004; G06T 7/001; G06T 7/10; G06T 7/11; G06T 7/12; G06T 7/136; G06T 7/337; G06T 7/30; G06T 7/32; G06T 7/33; G06T 7/38; G06T 7/73; G06T 2207/30108; G06T 2207/30128; G06K 9/6201; G06K 9/6203; G06K 9/6204; G06K 9/6206; G06K 9/6207; G06K 9/6209; G06K 9/621; G06K 9/6215; G06V 2201/06; G06V 20/66; G01N 21/9508

See application file for complete search history.

(56) References Cited

U.S. PATENT DOCUMENTS

| | | | |
|---|---|---|---|
| 2008/0135309 A1 | 6/2008 | Yuyama et al. | |
| 2014/0002631 A1* | 1/2014 | Amano | G06V 20/66 348/86 |
| 2015/0178674 A1 | 6/2015 | Yonaha et al. | |
| 2016/0109385 A1* | 4/2016 | Tanimoto | G01N 21/9508 356/432 |
| 2016/0114925 A1* | 4/2016 | Yuyama | B65B 57/16 382/141 |
| 2016/0210524 A1* | 7/2016 | Hasegawa | G06V 10/141 |
| 2017/0305589 A1 | 10/2017 | Yuyama et al. | |
| 2020/0175319 A1 | 6/2020 | Yokouchi | |

FOREIGN PATENT DOCUMENTS

| | | |
|---|---|---|
| CN | 107072881 A | 8/2017 |
| CN | 111052145 A | 4/2020 |
| JP | 9-81748 A | 3/1997 |
| JP | 2006-189354 A | 7/2006 |
| JP | 2010-190786 A | 9/2010 |
| JP | 2014-67342 A | 4/2014 |
| WO | WO 2016/047569 A1 | 3/2016 |

OTHER PUBLICATIONS

European Communication pursuant to Article 94(3) EPC for corresponding European Application No. 18809549.1, dated Nov. 11, 2021.
Nieves Santiago, "Attribute Data Treatment of Automated Inspection Vision System for Product Mix-Up Detection," Polytechnic University of Puerto Rico, 2012, 10 pages total.
Extended European Search Report for counterpart European Application No. 18809549.1 , dated Feb. 10, 2020.
International Preliminary Report on Patentability and Written Opinion of the International Searching Authority (Forms PCT/IB/326, PCT/IB/373, and PCT/ISA/237) for International Application No. PCT/JP2018/016282, dated Dec. 12, 2019, with English translation.
International Search Report (Form PCT/ISA/210) for International Application No. PCT/JP2018/016282, dated Jun. 19, 2018, with English translation.
The First Office Action and Search Report issued in counterpart Chinese Application No. 201880029204.4, dated Nov. 18, 2022, with English translation.

* cited by examiner

| MASTER IMAGE | | AFTER BREAKFAST | AFTER LUNCH | AFTER DINNER |
|---|---|---|---|---|
| (133) | 1ST DAY | | | MEDICINE PACKAGE No. 3 (133) |
| ATTRIBUTE INFORMATION | 2ND DAY | MEDICINE PACKAGE No. 1 (133) | MEDICINE PACKAGE No. 2 (133) | MEDICINE PACKAGE No. 6 (133) |
| MEDICINE CODE: XXX-XXXX<br>MEDICINE TYPE : TABLET<br>SHAPE : SPHEROID<br>DIMENSION: DIAMETER 10 mm<br>COLOR : WHITE<br>ENGRAVED STAMP: 133 | 3RD DAY | MEDICINE PACKAGE No. 4 (133) | MEDICINE PACKAGE No. 5 (133) | MEDICINE PACKAGE No. 9 (133) |
| | 4TH DAY | MEDICINE PACKAGE No. 7 (133) | MEDICINE PACKAGE No. 8 (133) | MEDICINE PACKAGE No. 12 (133) |
| | 5TH DAY | MEDICINE PACKAGE No. 10 (133) | MEDICINE PACKAGE No. 11 (133) | MEDICINE PACKAGE No. 15 (133) |
| | 6TH DAY | MEDICINE PACKAGE No. 13 (133) | MEDICINE PACKAGE No. 14 (133) | MEDICINE PACKAGE No. 18 (133) |
| | 7TH DAY | MEDICINE PACKAGE No. 16 (133) | MEDICINE PACKAGE No. 17 (133) | MEDICINE PACKAGE No. 21 (133) |
| | | MEDICINE PACKAGE No. 19 (133) | MEDICINE PACKAGE No. 20 (133) | |

⇐ PREVIOUS MEDICINE   [TO MENU]   NEXT MEDICINE ⇒

DISPENSING AUDIT SUPPORT APPARATUS AND DISPENSING AUDIT SUPPORT METHOD

CROSS-REFERENCE TO RELATED APPLICATIONS

The present application is a Continuation of PCT International Application No. PCT/JP2018/016282 filed on Apr. 20, 2018 claiming priority under 35 U.S.C § 119(a) to Japanese Patent Application No. 2017-106815 filed on May 30, 2017. Each of the above applications is hereby expressly incorporated by reference, in its entirety, into the present application.

BACKGROUND OF THE INVENTION

1. Field of the Invention

The present invention relates to a dispensing audit support apparatus and a dispensing audit support method, and in particular to a dispensing audit support apparatus and a dispensing audit support method which collate (compare) an image obtained by imaging medicine with a master image and support to audit whether the imaged medicine is in accordance with a prescription or not.

2. Description of the Related Art

In medical sites, commonly, a patient brings a prescription written by a medical doctor to a dispensing pharmacy, and medicines are dispensed according to the prescription in the dispensing pharmacy. At the time of the dispensing, so-called "one-dose packaging" is often performed to package the prescribed medicines in a packaging bag for each dose. When a pharmacist dispenses or provides medicines, the pharmacist is required to check prescribed contents based listed items in the prescription, patient information and the like, and the pharmacist bears heavily burden in the audit.

Therefore, in order to reduce the burden on pharmacists in the audit, dispensing audit support methods and dispensing audit support apparatuses have been developed to collate contents written in a prescription with contents of packaged medicines with regard to the kinds, quantity and the like of the medicines. For example, in Japanese Patent Application Laid-Open No. 2014-67342 (hereinafter referred to as "PTL 1"), discloses a technology which collates medicine master images with captured images to identify which medicines are present in the captured images and creates a listing table that displays the medicine master images and medicine area images showing each medicine identified in the captured images. According to PTL 1, this listing table can facilitate collation of the captured images with the master images and improve efficiency in visual audit by the pharmacist. Further, Japanese Patent Application Laid-Open No. 9-81748 (hereinafter, referred to as "PTL 2"), which relates to an apparatus for selecting a test article, discloses that influence of a rotational component is reduced by converting rectangular Cartesian coordinates to cylindrical coordinates and extracting contours, thereby performing the selection accurately.

CITATION LIST

PTL 1: Japanese Patent Application Laid-Open No. 2014-67342

PTL 2: Japanese Patent Application Laid-Open No. 9-81748

SUMMARY OF THE INVENTION

Collation (Comparison) between a captured image and a master image can be performed, for example, by setting a region of interest on the captured image, setting a template for the master image and collating the region of interest with the template. When performing such a collation, because the image includes distortion of a medicine shape, blur, inclusion of an end part and the like depending on collation conditions such as a position of a collation-target medicine in the image, it is necessary to appropriately set the region of interest and template according to the collation conditions in order to perform the collation with a high accuracy. With regard to this point, although a medicine master image and a captured image are collated in PTL 1 described above, it is not considered to set the region of interest and a template according to collation conditions. As for PTL 2, collation is performed not for contour but for an engraved stamp part in dispensing audit of medicine (tablets), and collation accuracy is not improved even if the engraved stamp part is converted to a cylindrical coordinate system because the engraved stamp changes according to a positional relationship with light sources. Thus, the collation accuracy is largely dependent on collation conditions in conventional techniques, and has low robustness.

The present invention has been made in view of such a situation, and aims to provide a dispensing audit support apparatus and a dispensing audit support method which is excellent in robustness in collation accuracy.

In order to achieve the above object, a dispensing audit support apparatus according to a first aspect of the present invention is provided with: a master image storing unit storing a master image showing a medicine; an imaging unit imaging an audit-target medicine to obtain a captured image; a medicine detecting unit detecting a position of the audit-target medicine in the captured image; a region-of-interest setting unit setting a region of interest on the image of the audit-target medicine, the region-of-interest setting unit setting a position, shape and size of the region of interest based on the detected position of the medicine; a template generating unit reading the master image showing a medicine written in a prescription from the master image storing unit and generating a template based on the read master image, the template generating unit setting a position, shape and size of the template according to the set region of interest; and a collating unit collating the template with the region of interest and outputting information indicating whether the audit-target medicine and the medicine shown by the master image are the same or not.

According to the first aspect, since the position, shape and size of the region of interest are set according to the position of the audit-target medicine (a collation-target medicine) in a captured image, and the position, shape and size of the master image are set according to the set region of interest, it is possible to avoid or reduce distortion of the medicine shape, blur, inclusion of the end part into the image, and the like due to the position of the audit-target medicine. Therefore, influence on collation accuracy by collation conditions is small, and it is possible to enhance robustness of the collation accuracy.

A dispensing audit support apparatus according to a second aspect is such that, in the first aspect, the region-of-interest setting unit sets the region of interest smaller as a distance between the detected position of the audit-target medicine and a center of the captured image is longer; and the template generating unit generates the template smaller as the set region of interest is smaller. When the distance between the audit-target medicine and the center of the captured image is long, problems such as that the audit-target medicine is imaged being distorted or blurred, and that the side surface of the medicine is included in the image may occur. When the region of interest and the template are set in sizes similar to sizes in a case where the distance is short, in such a situation, an area where the above problems occur is included in the region of interest and the template, and it is not possible to perform collation with a high accuracy. In collation, according to the second aspect, by setting the region of interest small and, furthermore, setting the template small according to the region of interest, it is possible to avoid the area where the above problems occur, and it is possible to perform collation with a high accuracy even in the case where the audit-target medicine is far away from the center of the captured image.

A dispensing audit support apparatus according to a third aspect is such that, in the first or second aspect, the region-of-interest setting unit sets the region of interest on the image of the audit-target medicine by causing the region of interest on the image of the audit-target medicine to move more in a direction to the center of the captured image as the distance between the detected position of the audit-target medicine and the center of the captured image is longer; and the template generating unit generates the template caused to move more relative to the master image as an amount of movement of the region of interest is larger. When the distance between the audit-target medicine and the center of the captured image is long, the image of the audit-target medicine may be imaged in a state that a side far from the center may be imaged larger than a side close to the center, being blurred. In this situation, when the region of interest and the template are set similarly to the case where the distance is short, it is not possible to perform collation with a high accuracy. In collation, by causing the region of interest to move and, furthermore, generating the template caused to move according to the amount of movement of the region of interest as in the third aspect, it is possible to avoid occurrence of significant blur, and it is possible to perform collation with a high accuracy even if the distance between the audit-target medicine and the center of the captured image is long.

A dispensing audit support apparatus according to a fourth aspect is such that, in any one of the first to third aspects, the region-of-interest setting unit causes the position of the region of interest on the captured image to move based on a direction of illumination onto the audit-target medicine; and the template generating unit causes the position of the template for the master image to move according to the region of interest being caused to move. Even if it becomes difficult to grasp characteristics of the medicine due to a relationship with illumination at the time of collation, and the collation accuracy decreases, it is possible to, by causing the position of the region of interest to move and causing the position of the template to move according to the movement of the region of interest as in the fourth aspect, avoid occurrence of such a problem, and it is possible to perform collation with a high accuracy.

A dispensing audit support apparatus according to a fifth aspect is such that, in any one of the first to fourth aspects, the region-of-interest setting unit and the template generating unit set the region of interest and the template to be in shapes similar to the audit-target medicine, respectively, if the distance between the position of the audit-target medicine and the center of the captured image is equal to or below a threshold, and set the region of interest and the template to be in rectangular shapes, respectively, if the distance between the position of the audit-target medicine and the center of the captured image exceeds the threshold. If the audit-target medicine is near the center of the captured image (if the distance is equal to or below the threshold), the shape of the medicine in the captured image is close to the true shape of the medicine, and, therefore, the region of interest and the template are in shapes similar to the shape of the audit-target medicine. However, if the audit-target medicine is far away from the center of the captured image (if the distance exceeds the threshold), the problems such as that the shape of the medicine is distorted in the captured image or that the end part (side surface) is imaged in the image may occur. In collation, by setting the region of interest and setting the template according to the region of interest as in the fifth aspect, it is possible to avoid occurrence of such problems, and it is possible to perform collation with a high accuracy.

A dispensing audit support apparatus according to a sixth aspect is such that, in any one of the first to fifth aspects, the collating unit performs the collation by turning at least one of the region of interest and the template to cause orientations of the region of interest and the template to correspond to each other. According to the sixth aspect, it is possible to perform accurate collation by causing the orientations of the region of interest and the template to correspond to each other.

A dispensing audit support apparatus according to a seventh aspect is such that, in any one of the first to sixth aspects, the collating unit performs the collation by magnifying or reducing at least one of the region of interest and the template to cause sizes of the region of interest and the template to correspond to each other. According to the seventh aspect, it is possible to perform accurate collation by causing the sizes of the region of interest and the template to correspond to each other.

A dispensing audit support apparatus according to an eighth aspect is such that, in any one of the first to seventh aspects, each of the template and the region of interest includes an engraved stamp area showing an engraved stamp provided on the medicine. The engraved stamp provided on the medicine is effective as a clue for collation. By each of the region of interest and the template including the engraved stamp area as in the eighth aspect, it is possible to perform accurate collation.

A dispensing audit support apparatus according to a ninth aspect is such that, in any one of the first to eighth aspects, the master image is an image based on an image obtained by imaging the audit-target medicine by the imaging unit under lighting used when the collation is performed. In the ninth aspect, since the image based on the image obtained by imaging the audit-target medicine under lighting used at the time of collation by the imaging unit, is used as the master image, it is possible to cause the illumination at the time of imaging the master image and the illumination at the time of collation to correspond to each other. Accordingly, it is possible to obtain an appropriate master image and improve collation accuracy.

In order to achieve the above object, a dispensing audit support method according to a tenth aspect of the present invention is a dispensing audit support method by a dispensing audit support apparatus comprising a master image storing unit storing a master image showing a medicine, and an imaging unit imaging an audit-target medicine to obtain a captured image, the method including: a medicine detecting process of the dispensing audit support apparatus detecting a position of the audit-target medicine in the captured image; a region of interest setting process of the dispensing audit support apparatus setting a region of interest on the image of the audit-target medicine, wherein a position, shape and size of the region of interest are set based on the detected position of the medicine; a template generating process of the dispensing audit support apparatus reading the master image showing a medicine written in a prescription from the master image storing unit and generating a template according to the region of interest based on the read master image; and a collating process of the dispensing audit support apparatus collating the template and the region of interest and outputting information indicating whether the medicine shown by the captured image and the medicine shown by the master image are the same or not. According to the tenth aspect, as in the first aspect, the influence on the collation accuracy due to the position of the collation-target medicine is small, and it is possible to increase the robustness of the collation accuracy. Note that a program that causes the dispensing audit support apparatus (a computer) to execute the dispensing audit support method according to the tenth aspect, and a non-transitory recording medium in which a computer-readable code of the program is recorded are also given as aspects of the present invention.

As described above, according to the dispensing audit support apparatus and the dispensing audit support method of the present invention, it is possible to increase the robustness of the collation accuracy.

BRIEF DESCRIPTION OF THE DRAWINGS

FIG. 7 is a diagram showing a master image and attribute information about a medicine.

FIG. 13 is a diagram showing a display example of a collation result.

DESCRIPTION OF THE PREFERRED EMBODIMENTS

An embodiment of a dispensing audit support apparatus and a dispensing audit support method according to the present invention will be described below in detail with reference to accompanying drawings.

First Embodiment

Figure 1:
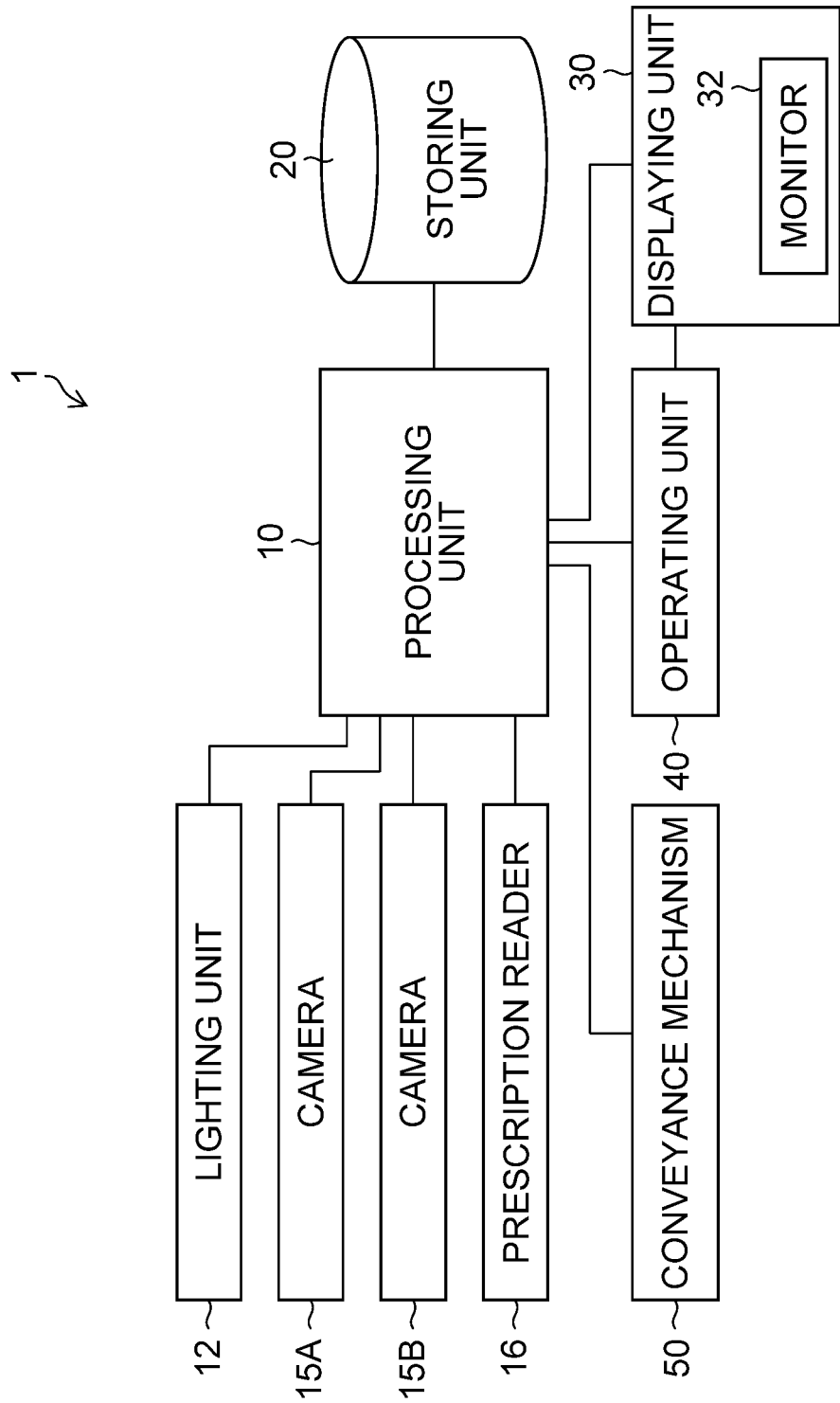
FIG. 1 is a block diagram showing a configuration of a dispensing audit support apparatus according to one embodiment of the present invention.

FIG. 1 is a diagram showing a configuration of a dispensing audit support apparatus 1 (dispensing audit support apparatus) according to an embodiment of the present invention. The dispensing audit support apparatus 1 includes: a processing unit (processor) 10 (imaging unit, medicine detecting unit, region-of-interest setting unit, template generating unit and collating unit); a storing unit 20 (master image storing unit); a displaying unit 30; an operating unit 40 and a conveyance mechanism 50. A lighting unit 12, a camera 15A (imaging unit), a camera 15B (imaging unit) and a prescription reader 16 are connected to the processing unit 10.

Figure 2:
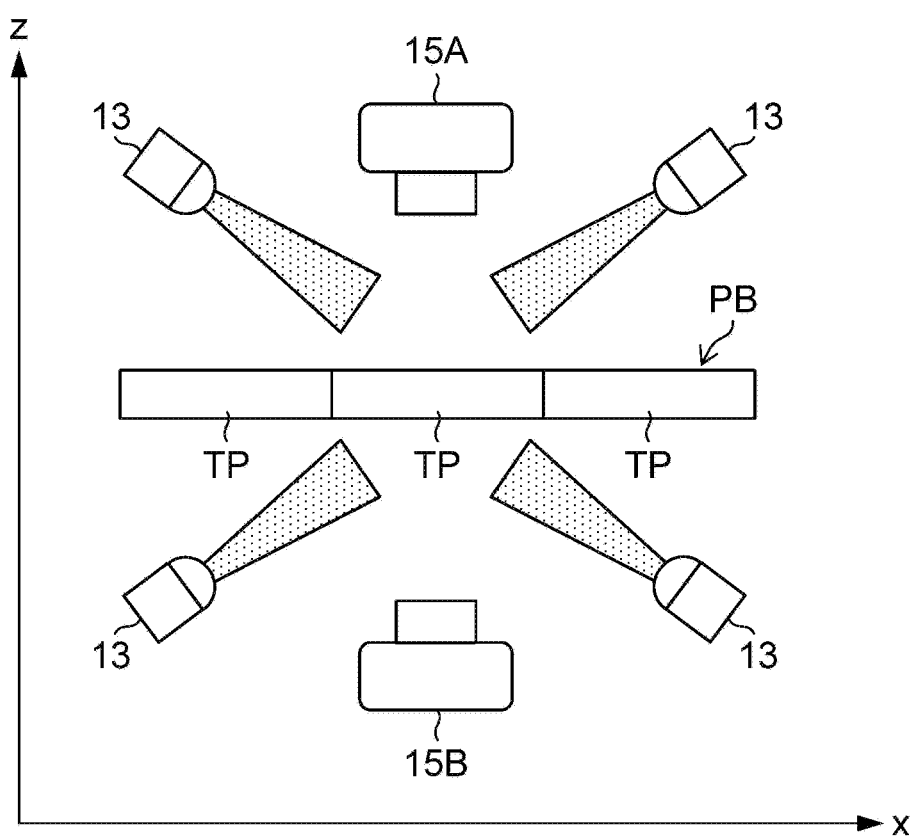
FIG. 2 is a diagram showing a state when obtaining an image of a packing bag under lighting.
Figure 3:
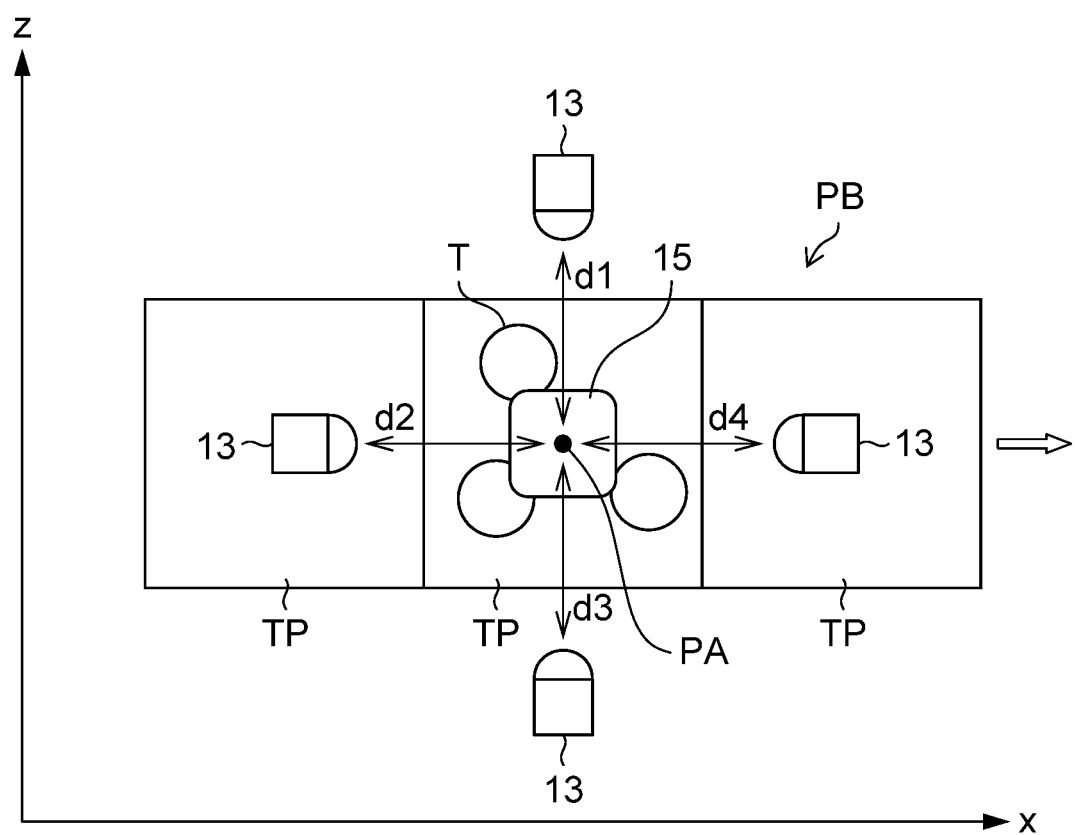
FIG. 3 is another diagram showing a state when obtaining an image of a packing bag under lighting.

Each of the camera 15A and the camera 15B includes a digital camera. As shown in FIG. 2, the camera 15A is arranged on an upper side (+Z side in FIG. 2) of a medicine strip package PB which includes packaging bags TP (medicine packages) formed on series, and the camera 15B is arranged on a lower side (−Z side in FIG. 2) of the medicine strip package PB, and medicines packaged in each packaging bag TP are imaged from above and below (plurality of different directions). The packaging bags TP (medicine strip package PB) are conveyed by the conveyance mechanism 50 in a +X direction in FIG. 2 (axis along a longitudinal direction of the medicine strip package PB). At the time of imaging, a plurality of light sources 13 provided to the lighting unit 12 illuminate the packaging bag TP from four directions (±X directions and ±Y directions) on the upper and lower sides, respectively. In FIG. 3, distances (d1, d2, d3 and d4) between each of the plurality of light sources 13 and an imaging optical axis PA of the cameras 15A and 15B are the same. That is, the plurality of light sources 13 are disposed at equal intervals (d1=d2=d3=d4) from the imaging optical axis PA.

The prescription reader 16 reads out prescription information. For example, the prescription reader 16 reads information such as a patient name, prescribed medicines, a quantity of the medicines and the like from a prescription written on paper by OCR (optical character recognition). If a bar code or the like indicating the information about the prescribed medicines is recorded on the prescription, information about the prescribed medicines, the quantity of the medicines and the like may be read out from the bar code. Further, a user may read out the prescription and input prescription information though an input device such as a keyboard provided to the operating unit 40.

<Configuration of Processing Unit>

Figure 4:
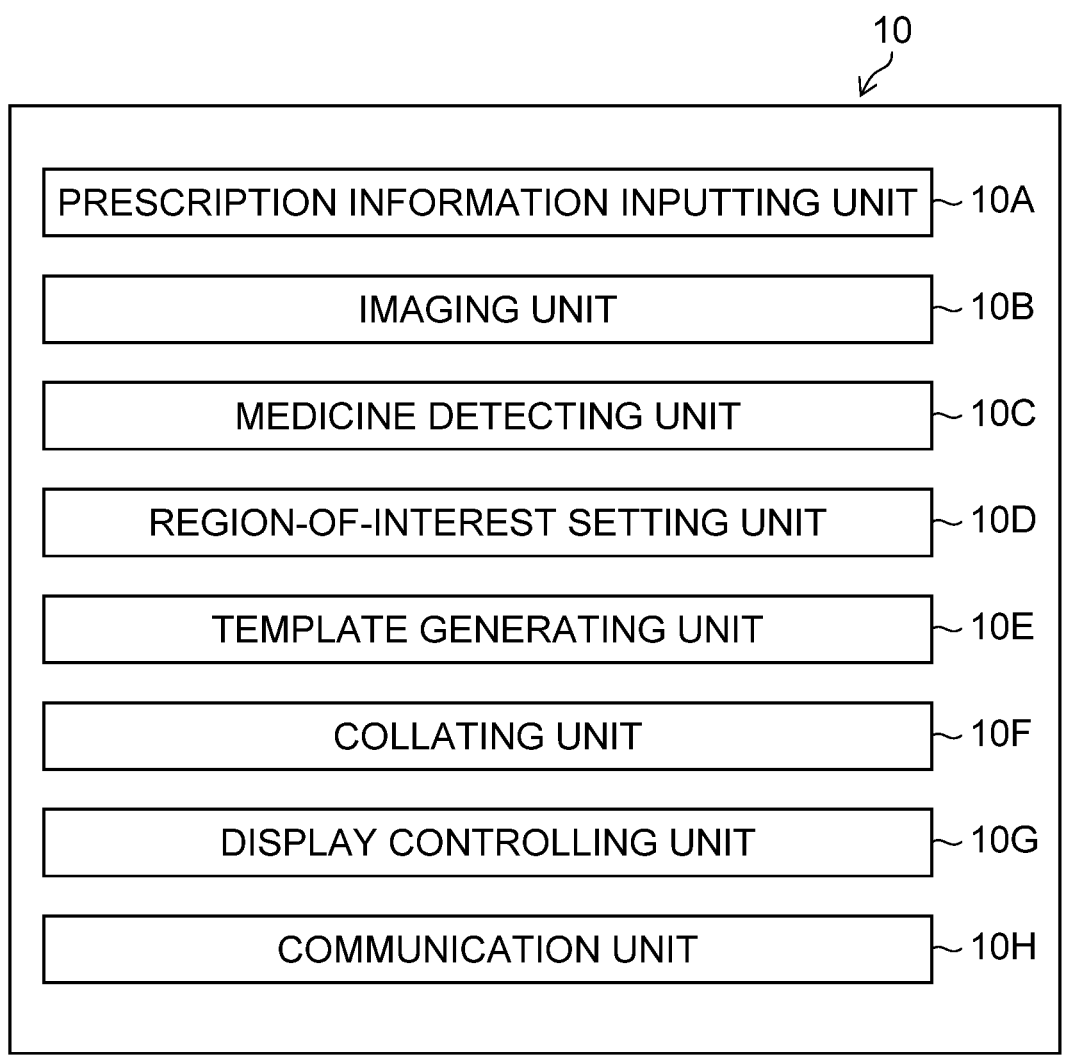
FIG. 4 is a diagram showing a functional configuration of a processing unit.

FIG. 4 is a diagram showing a functional configuration of the processing unit 10. The processing unit 10 is provided with a prescription information inputting unit 10A, an imaging unit 10B (imaging unit), a medicine detecting unit 10C (medicine detecting unit), a region-of-interest setting unit 10D (region-of-interest setting unit), a template generating unit 10E (template generating unit), a collating unit 10F (collating unit), a display controlling unit 10G and a communication unit 10H. Functions of these units are realized by devices such as a CPU (Central Processing Unit) and various kinds of electronic circuits through referring to data stored in an EEPROM (Electronically Erasable and Programmable Read Only Memory; a non-transitory recording medium) or the like. Further, those functions are performed by executing a dispensing audit support program stored in a ROM (Read Only Memory; a non-transitory recording medium) or the like. When performing processes, a RAM (Random Access Memory) or the like is used as a temporary storage area and a working area. Note that illustrations of those devices such as the CPU are omitted in FIG. 4.

The prescription information inputting unit 10A controls the prescription reader 16 to input information described in the prescription (for example, a patient's name, identification information and a quantity of medicine, direction for use, and the like). The imaging unit 10B controls the camera 15A and the camera 15B to image the audit-target medicines packaged in each of the packaging bags TP and obtain a captured image. The medicine detecting unit 10C detects a position of the audit-target medicine in the captured image obtained by the imaging unit 10B. In addition to the position of the audit-target medicine, its orientations may be detected. The region-of-interest setting unit 10D sets a position, shape and size of a region of interest for the image of the audit-target medicine, based on the position detected by the medicine detecting unit 10C. The template generating unit 10E reads a master image showing a medicine written in the prescription based on the information read by the prescription information inputting unit 10A and generates a template based on the read master image. The collating unit 10F collates the template with the region of interest and outputs information indicating whether the audit-target medicine and the medicine shown by the master image are the same or not. The display controlling unit 10G performs display control for a collation result and the like. The communication unit 10H communicates with a server, a database and the like, not shown, via a network to obtain master images of medicines and information of medicine such as attribution information. A detailed process of the dispensing audit support method by these functions is to be described later.

The functions of the processing unit 10 described above can be realized using various kinds of processors. The various kinds of processors include, for example, a CPU (Central Processing Unit) that is a general-purpose processor that executes software (a program) to realize various kinds of functions. Further, the various kinds of processors may include a programmable logic device (PLD) such as an FPGA (Field Programmable Gate Array) and the like, which is a processor capable of changing circuit configuration after being manufactured. Furthermore, the various kinds of processors may include a dedicated electrical circuit such as an ASIC (Application Specific Integrated Circuit) or the like, which is a processor having a circuit configuration specially designed for performing specific processes.

The functions of each unit may be realized by a single processor or may be realized by combination of a plurality of processors. Further, a plurality of functions may be realized by a single processor. As an example of a case where a plurality of functions is realized by one processor, first, there is a mode in which a single processor is configured with a combination of one or more CPUs and software, and the processor realizes the plurality of functions, as is represented by a computer such a client and a server. Secondly, there is a mode employing a processor that realizes the functions of the whole system by a single IC (Integrated Circuit) chip, as is represented by a system on chip (SoC). As described above, as for a hardware structure, the functions of each unit may be configured using one or more of the various kinds of processors described above. Further, for operating those processors, a computer-readable codes of a program for causing the dispensing audit support apparatus (computer) to perform the dispensing audit support method according to the present invention are recorded in a non-transitory recording medium, not shown, such as the ROM (Read-Only Memory).

<Configuration of Storing Unit>

Figure 5:
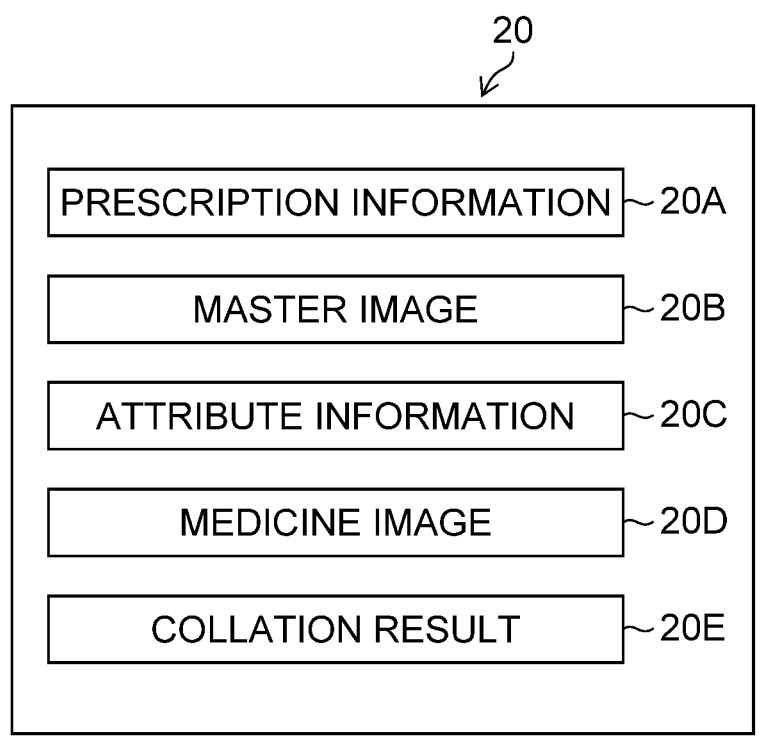
FIG. 5 is a diagram showing information stored in a storing unit.

The storing unit 20 is configured with a non-transitory recording medium such as a CD (Compact Disc), a DVD (Digital Versatile Disc), a hard disc and various kinds of semiconductor memories, and a controlling unit therefor, and stores images and information shown in FIG. 5 with associating them with one another. Prescription information 20A is information read out via the prescription reader 16. The prescription information 20A includes, for example, a patient's name, identification information, a quantity of medicine, direction for use of each medicine, and the like. A master image 20B is a master image of each medicine or a processed master image which is obtained by image-processing the master image. As attribute information 20C, a medicine type, shape, size, color, engraved stamp and the like of each medicine are given, but the attribute information 20C is not limited thereto. A medicine image 20D is a captured image and/or an image of audit-target medicine extracted from the captured image. A collation result 20E is information indicating a collation result created by the processing unit 10. In addition to these images and information, information about a region of interest and/or a template may be stored in the storing unit 20. At the time of processing by the processing unit 10, reading and writing of these images and information are performed between the processing unit 10 and the storing unit 20.

<Configurations of Displaying Unit and Operating Unit>

The displaying unit 30 is provided with a monitor 32 and can display prescription information read out via the prescription reader 16, an image of packaged medicines, information and images stored in the storing unit 20, the collation result and the like. The operating unit 40 includes a pointing device such as a mouse and an input device such as a keyboard. The user can operate an image, a button and the like displayed on the monitor 32 with the operating unit 40.

<Process of Dispensing Audit Support Method>

Figure 6:
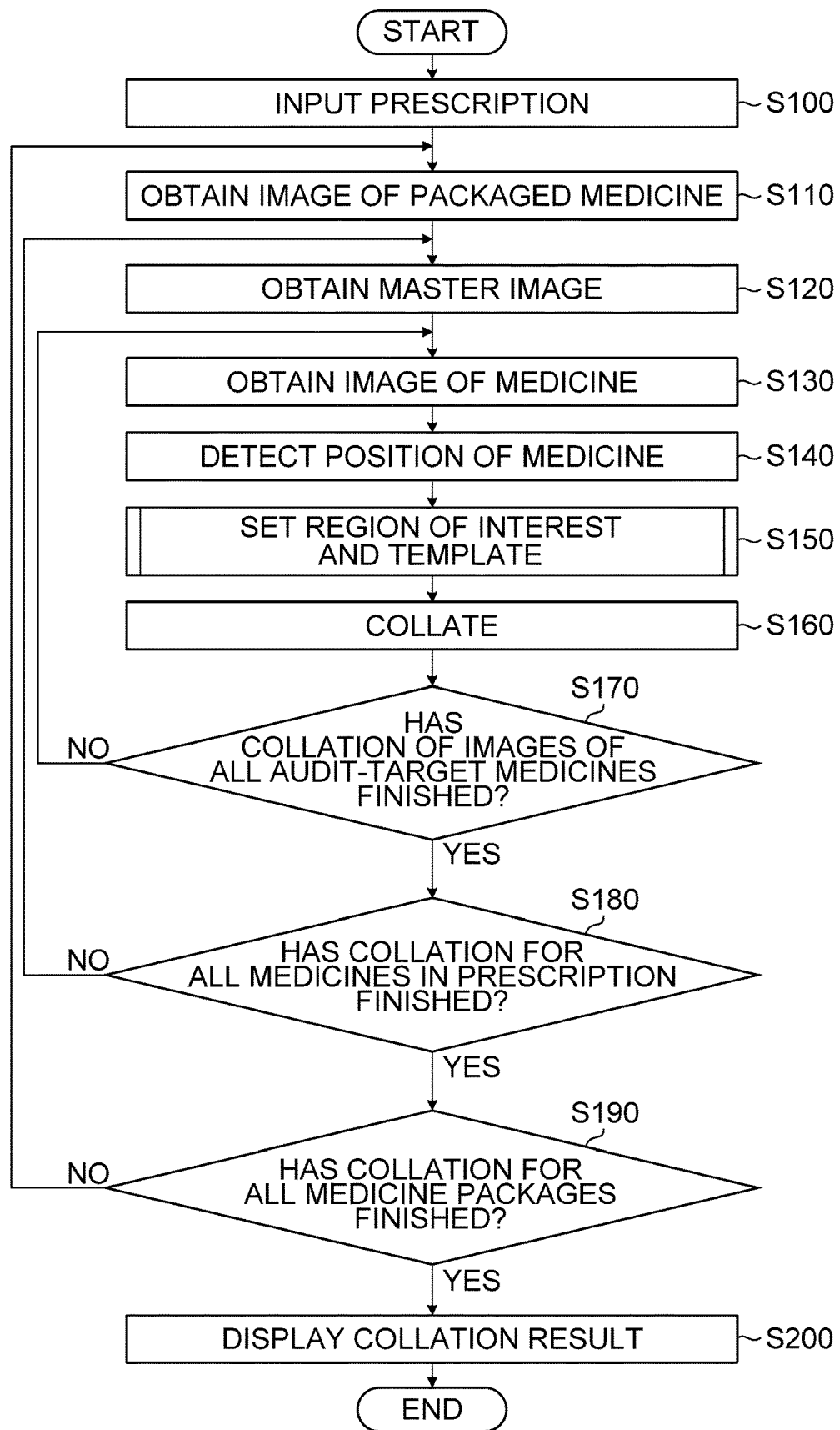
FIG. 6 is a flowchart showing processes of a dispensing audit support method.

A processes of the dispensing audit support method by the dispensing audit support apparatus 1 having the configuration described above will be described. FIG. 6 is a flowchart showing processes of the dispensing audit support method.

At step S100, prescription information is inputted by the prescription reader 16 and the processing unit 10 (prescription information inputting unit 10A). Alternatively, the prescription information 20A stored in the storing unit 20 may be read out. At step S110, the imaging unit 10B controls the cameras 15A and 15B to image medicines packaged in a packaging bag TP of the medicine strip package PB from a plurality of directions (up and down directions) to obtain an image.

At step S120, a master image of a medicine written in the prescription is obtained based on the prescription information read at step S100. The obtained master image may be the master image 20B stored in the storing unit 20 or an image obtained from an external medicine database or the like via the processing unit 10 (communication unit 10H).

The image obtained as the master image may be an image (image obtained by image-processing the captured image) based on an image obtained by imaging an audit-target medicine under the light sources 13 (light sources of lighting which are used at the time of collation) by the cameras 15A and 15B and the processing unit 10 (imaging unit 10B). In this case, it is preferable to use an image based on an image imaged near a center of visual field center of each of the cameras 15A and 15B, as the master image.

Figure 7:
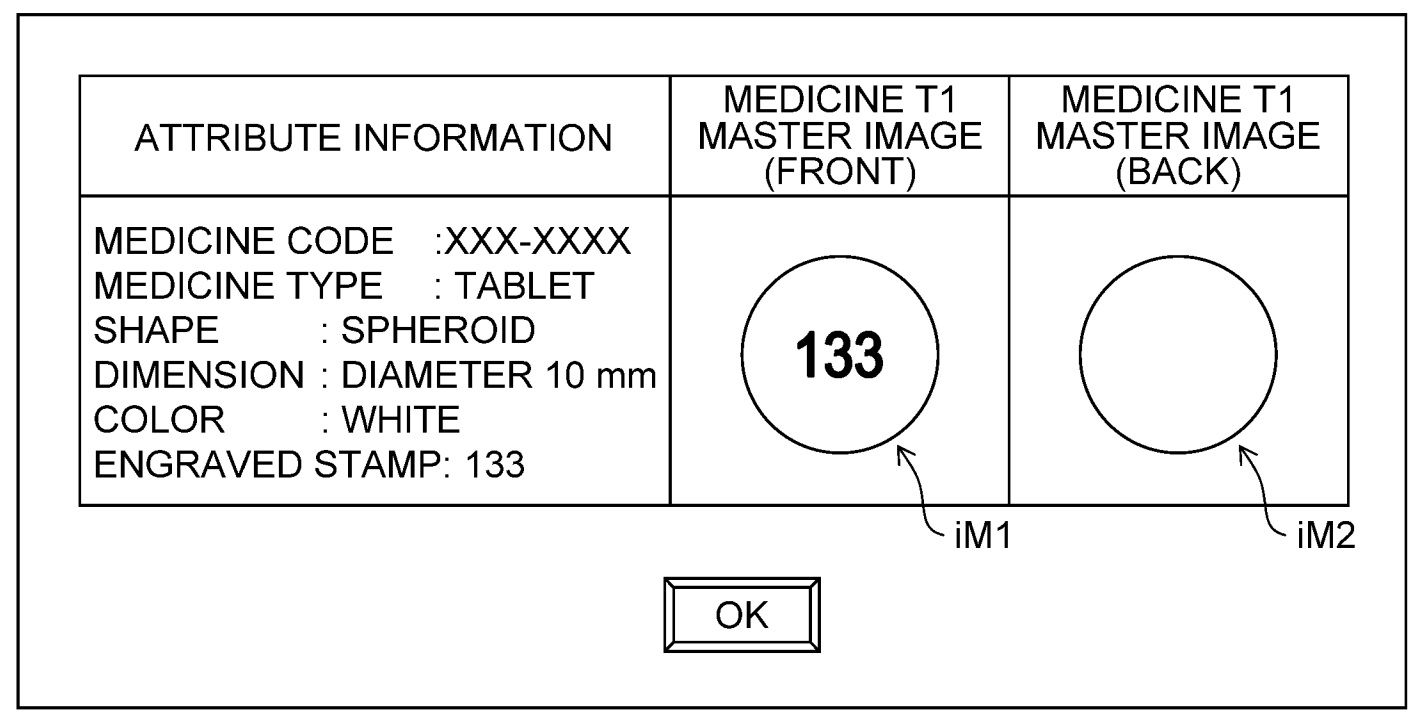

FIG. 7 shows an example of the master image which includes a plurality of images (master images iM1 and iM2) obtained by imaging a medicine T1 from different directions (up and down directions of the medicine). The master image iM1 is an image of a front surface of the medicine T1, and the master image iM2 is an image of a back surface of the medicine. In the example of FIG. 7, attribute information (attribute information 20C; see FIG. 5) indicating attributes of the medicine T1 is associated with the master images iM1 and iM2. The processing unit 10 (display controlling unit 10G) displays the master images and attribute information on the monitor 32 in response to a user operation via the operating unit 40.

The processing unit 10 (medicine detecting unit 10C) extracts a medicine area of each medicine from the captured image, performs image-processing such as magnification or reduction and brightness adjustment as necessary, and obtains an image of each individual medicine (step S130; medicine detecting process). After obtaining the image of each individual medicine, the processing unit 10 (medicine detecting unit 10C) detects a position of an audit-target medicine in the captured image (step S140; medicine detecting process). At step S140, for example, an edge of the medicine is detected to determine a center of the medicine, and a position of the determined center can be detected as the position of the audit-target medicine.

<Setting of Region of Interest and Template>

The processing unit 10 (region-of-interest setting unit 10D and template generating unit 10E) sets a region of interest and a template based on the position detected at step S140 (step S150; region of interest setting process and template generating process). Setting of the region of interest and the template at step S150 will be described below with reference to a flowchart of FIG. 8.

At step S151, the processing unit 10 (region-of-interest setting unit 10D) calculates a distance between the medicine and a center of the captured image based on the position of the medicine detected at step S150 and determines whether or not the calculated distance is equal to or below a threshold (step S152). If a positive determination result is obtained (step S152: YES), the processing unit 10 (region-of-interest setting unit 10D) sets the region of interest to be in a shape similar to the audit-target medicine (step S153; region of interest setting process). Further, the processing unit 10 (template generating unit 10E) sets the template for the master image to be in a shape similar to the audit-target medicine according to the shape of the region of interest (step S154: template generating process). Being in "a shape similar to the audit-target medicine" means that, for example, the region of interest (or template) is in a circular shape with a different size if the medicine is in a circular shape, and the region of interest (or template) is in an oval shape with a different size if the medicine is in an oval shape.

On the other hand, if a negative determination result is obtained at step S152 (if the calculated distance exceeds the threshold), the processing unit 10 (region-of-interest setting unit 10D) sets the region of interest to be in a rectangular shape (step S155; region of interest setting process) and sets the template for the master image to be in a rectangular shape according to the rectangular region of interest (step S156; template generating process).

When the shapes of the region of interest and the template are set by the processes up to step S156, the processing unit 10 (region-of-interest setting unit 10D) moves the position of the region of interest in a direction to the center of the captured image and sets the region of interest in such a manner that the larger the distance between the medicine and the center of the captured image is, the more the position of the region of interest is moved and the smaller the size of the region of interest is set (step S157: region of interest setting process). The size of the region of interest can be set, for example, to "r×sin θ", "0.5×r×sin θ" or the like when a radius of the medicine is designated by r, and an angle formed by the medicine and the imaging optical axis PA is designated by θ. The processing unit 10 (template generating unit 10E) generates a template at a position, with a size and a shape corresponding to the position, size and shape of the region of interest (step S158; template generating process).

<Influence on Collation Due to Relationship Between Position of Medicine and Light Sources>

The processes of steps S151 to S158 will be further described. If it is assumed that the medicine T1 has a three-dimensional structure as in a cross-sectional view of FIG. 9 (having a thickness and formed by a curved surface), when the medicine T1 exists at a position away from the center of the visual field (imaging optical axis PA) (in FIG. 9, in the −X direction), the influence of light L from the light source in the −X direction becomes the strongest among the light sources 13 (see FIG. 3). Considering this light L, shadows are formed for engraved stamps F2 and F3 in FIG. 9 because the light L is obliquely incident on the engraved stamps F2 and F3. However, as for an engraved stamp F1, since the light L is incident on the engraved stamp F1 from almost directly above, a shadow is not formed almost at all. Therefore, when the medicine T1 is imaged from above with the imaging optical axis PA (see FIG. 3) positioned at a center, the engraved stamp F1 is blurred, whereas the engraved stamps F2 and F3 are clear. Therefore, when the position, size and shape of the region of interest are fixed regardless of the position of the medicine, collation is performed in a state in which the blurred engraved stamp F1 is included. This may cause an erroneous collation result due to mismatch in engraved stamps between the template that is based on the master image imaged near the visual field center (in which engraved stamps are not blurred) and the captured image.

Figure 9:
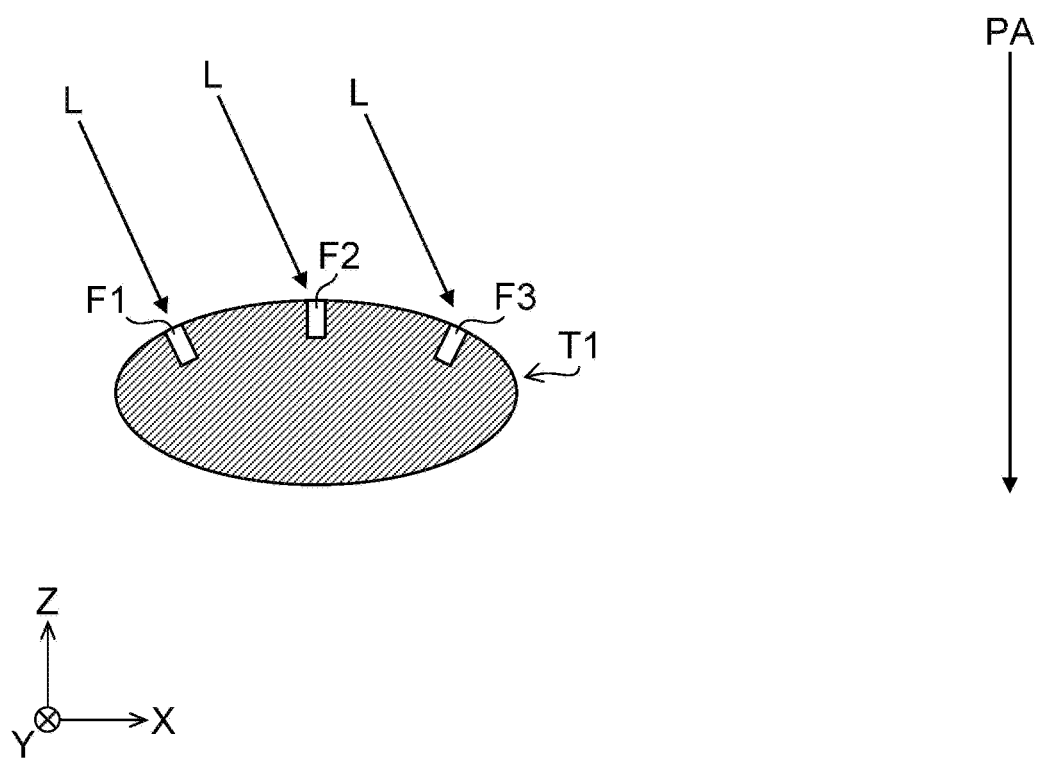
FIG. 9 is a diagram showing a blur of an engraved stamp due to a shape of a medicine.

When the position of the medicine T1 is far away from the center of the captured image, the shape of the medicine T1 is distorted in the captured image, and, in addition, a side surface of the medicine T1 (side close to the center of the captured image; on a right side in FIG. 9) is taken in the captured image. Therefore, when the position, size and shape of the region of interest are fixed regardless of the position of the medicine, collation is performed in a state in which the distorted area and an unnecessary area are included. This may cause an erroneous collation result in the collation between the template that is based on the master image imaged near the visual field center (in which there is no distortion, and the side surface is not included) and the captured image.

Therefore, in the first embodiment, the position, size and shape of the region of interest are set based on the position of the medicine so that a blurred area (in FIG. 9, part of the engraved stamp F1) and the side surface of the medicine are not included in the region of interest. Then, the position, size and shape of the template are set according to the region of interest. Examples of setting the region of interest and the template will be specifically described below.

Example of Setting of Region of Interest

Figure 10A:
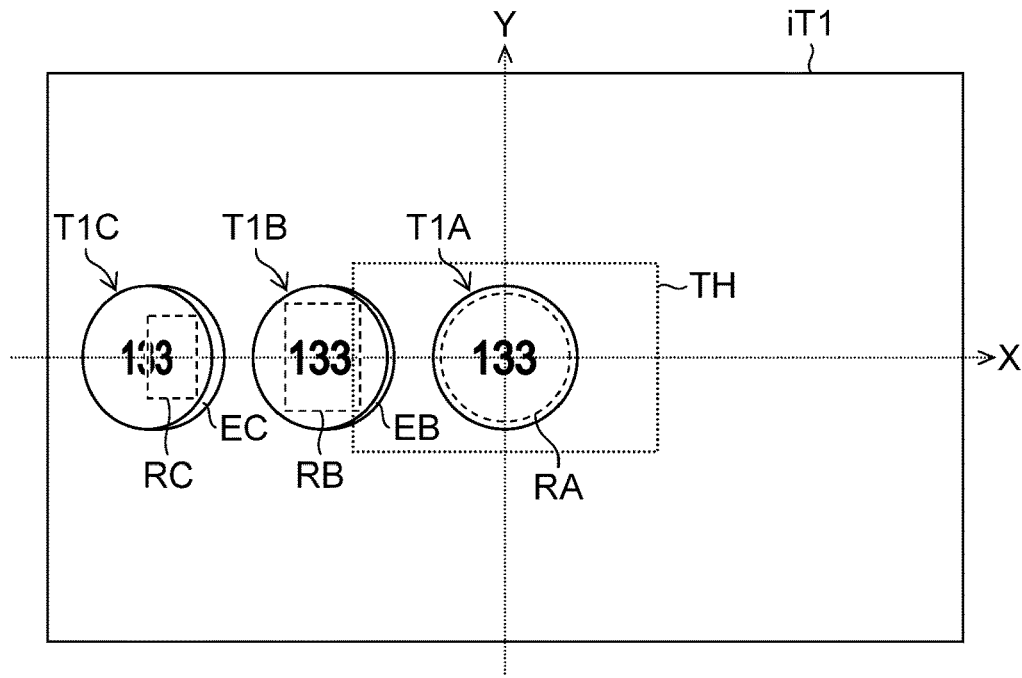
FIG. 10A is a diagram showing setting of the region of interest according to a position of a medicine.
Figure 10B:
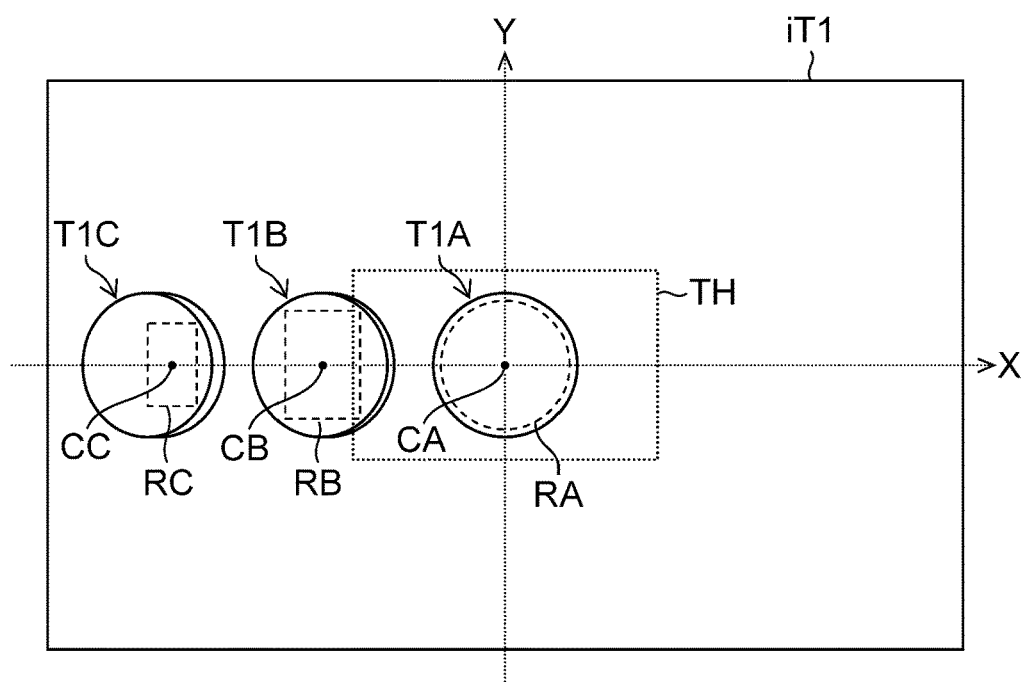
FIG. 10B is a diagram showing setting of the region of interest according to the position of the medicine.

FIGS. 10A and 10B are diagrams showing an example of setting of the region of interest based on a position of a medicine. FIG. 10A shows an example of setting of the region of interest when the medicine T1 exists on a center part, an intermediate part and an end part (designated by reference symbols T1A, T1B and T1C, respectively) of the captured image iT1 (obtained by imaging a packaging bag TP from the +Z direction). Specifically, in the case of a medicine T1A (medicine T1 exists in a center of the captured image iT1), the processing unit 10 (region-of-interest setting unit 10D) sets a region of interest RA to be in a circular shape similar to the medicine T1A (in a circular shape). The region of interest RA includes an engraved stamp area showing an engraved stamp "133". In the case of a medicine T1B (medicine T1 exists at the intermediate part in the −X direction in the captured image iT1), the processing unit 10 (region-of-interest setting unit 10D) sets a region of interest RB having a rectangular shape (smaller in size than the region of interest RA) such that the region of interest RB does not include the −X side area and a side surface area EB. The region of interest RB also includes an engraved stamp area showing an engraved stamp "133". Here, in FIGS. 10A and 10B, it is assumed that ⅓ (one-third) of a distance from the center to end part of the captured image iT1 is a threshold (value is a mere example) in each of the ±X directions and ±Y directions, and it is assumed that a position of the medicine T1B is beyond the threshold in the X axis direction and in the Y axis direction.

In the case of a medicine T1C (medicine T1 exists at an end part in the −X direction in the captured image iT1), a side surface area EC is taken largely in the captured image, and a "1" part which is close to the light source on the −X side is significantly blurred in the engraved stamp "133". Therefore, the processing unit 10 (region-of-interest setting unit 10D) sets a region of interest RC having a rectangular shape (smaller in size than RB) so as to avoid the side surface area EC and the "1" part of the engraved stamp. The region of interest RC includes a part showing "33" in the engraved stamp area showing the engraved stamp "133".

FIG. 10B is a diagram showing positions of centers CA, CB and CC of the regions of interest RA, RB and RC. The center CA is at a center of the medicine T1A, that is, the center of the captured image iT1. The centers CB and CC are moved to the center side (+X side) of the captured image iT1 (an amount of movement of the center CC> an amount of movement of the center CB). Note that illustration of the engraved stamps are omitted in FIG. 10B.

Figure 8:
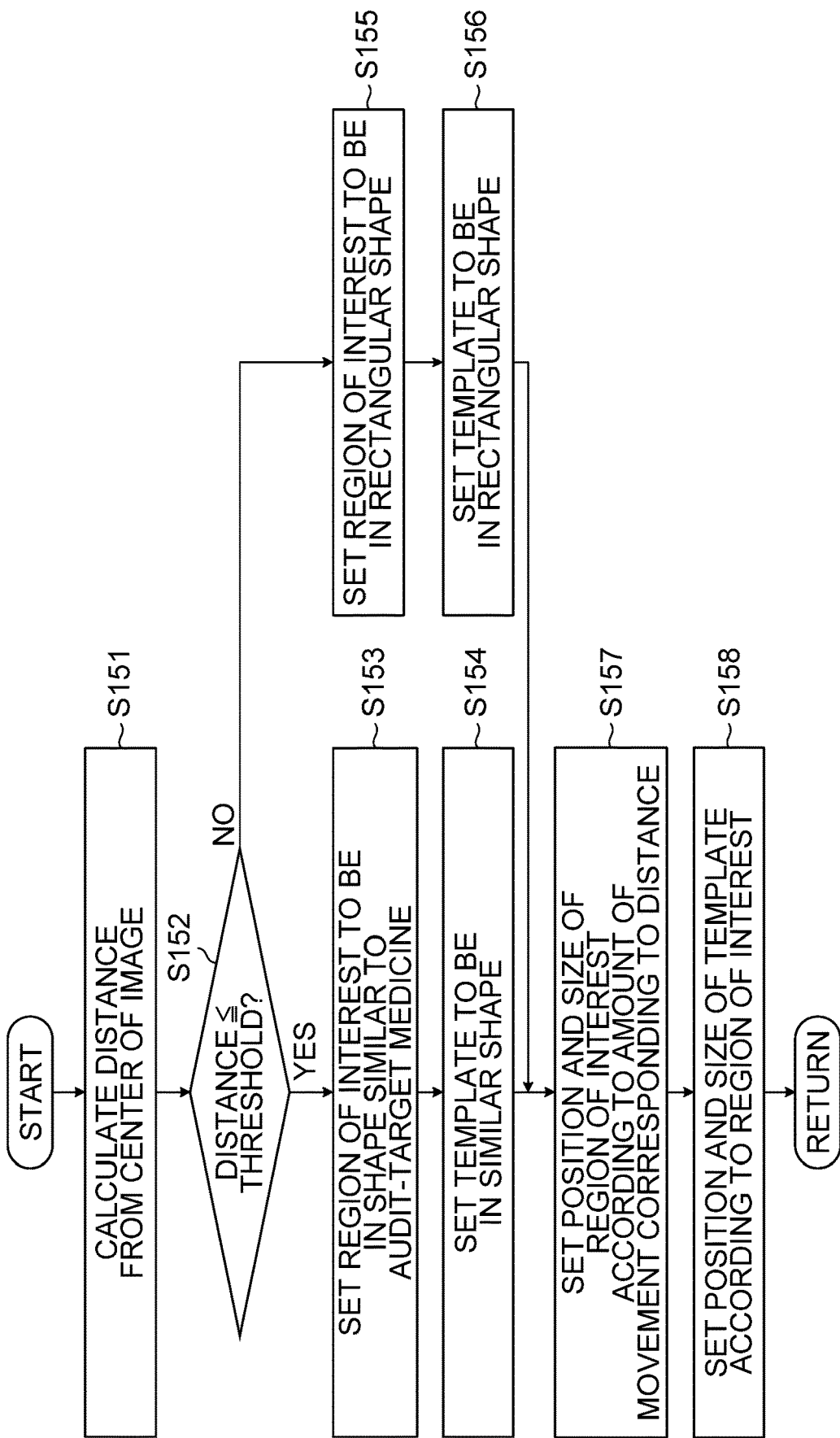
FIG. 8 is a flowchart showing processes of setting a region of interest and a template.

The processing unit 10 (template generating unit 10E) sets the position, shape and size of the template according to the region of interest set in this way (step S158 in FIG. 8; template generating process). Specifically, the smaller the region of interest is, the smaller the template is generated. The larger the amount of movement of the region of interest is, the more the template for the master image is moved. The template is moved in the same direction as a movement direction of the region of interest relative to the light sources. Here, the processing unit 10 (template generating unit 10E) generates the template that includes an engraved stamp area showing an engraved stamp (or part of the engraved stamp).

Figure 11A:
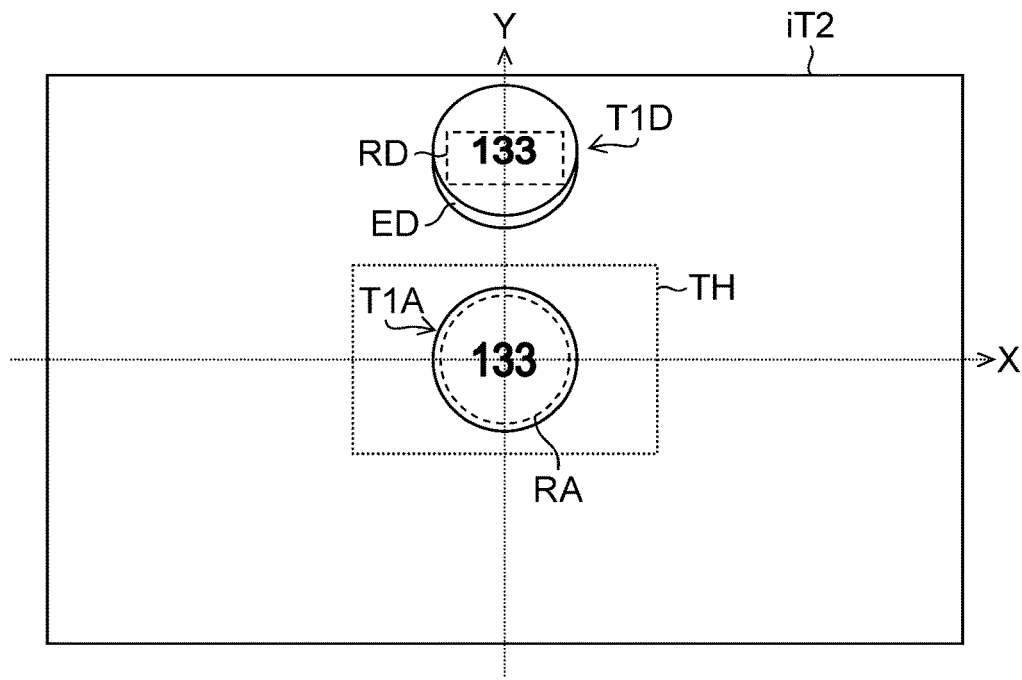
FIG. 11A is another diagram showing setting of the region of interest according to the position of the medicine.
Figure 11B:
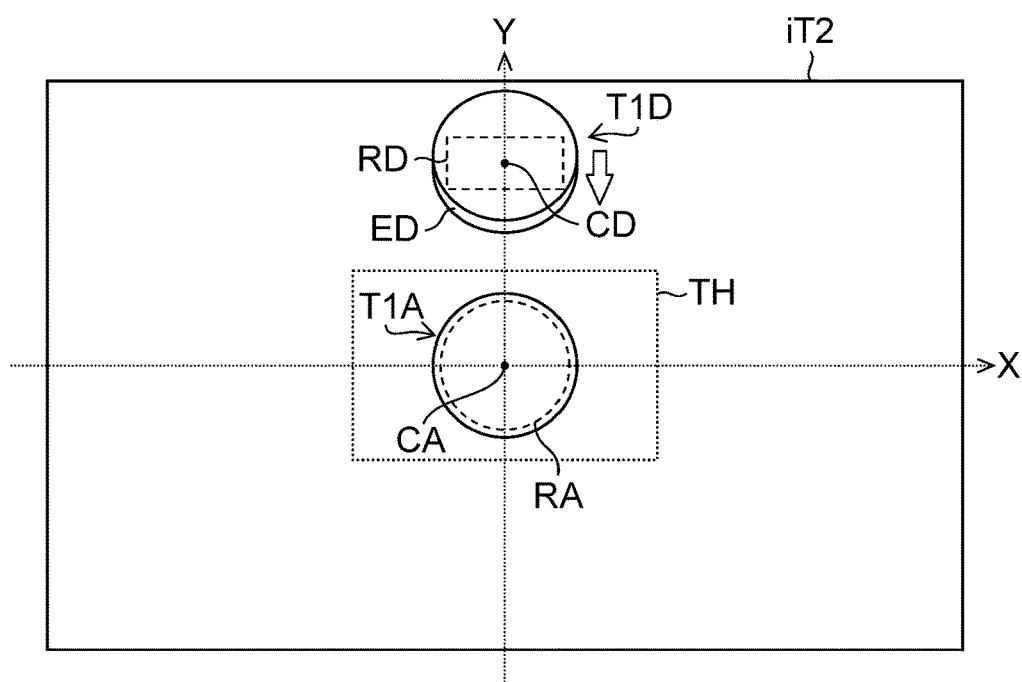
FIG. 11B is another diagram showing setting of the region of interest according to the position of the medicine.

FIGS. 11A and 11B are diagrams showing setting of region of interest when the medicine T1 exists on a center part and an end part in the +Y direction (designated by reference symbols T1A and T1D, respectively). In FIG. 11A, for the medicine T1A, the processing unit 10 (region-of-interest setting unit 10D) sets the region of interest RA having a circular shape (shape similar to the medicine T1), similarly to FIGS. 10A and 10B. As for the medicine T1D (medicine T1 exists at the end part in the +Y direction in a captured image iT2), the processing unit 10 (region-of-interest setting unit 10D) sets a region of interest RD having a rectangular shape (smaller in size than the region of interest RA) such that the region of interest RD does not include an area on a +Y side (area strongly influenced by the light source on the +Y side) and a side surface area ED.

FIG. 11B is a diagram showing positions of centers CA and CD of the regions of interest RA and RD. The center CA is on the center of the medicine T1A (that is, the center of the captured image) similarly to FIG. 10B, and the center CD is moved to the center side (−Y side; direction shown by an arrow) on the captured image.

Figure 12A:
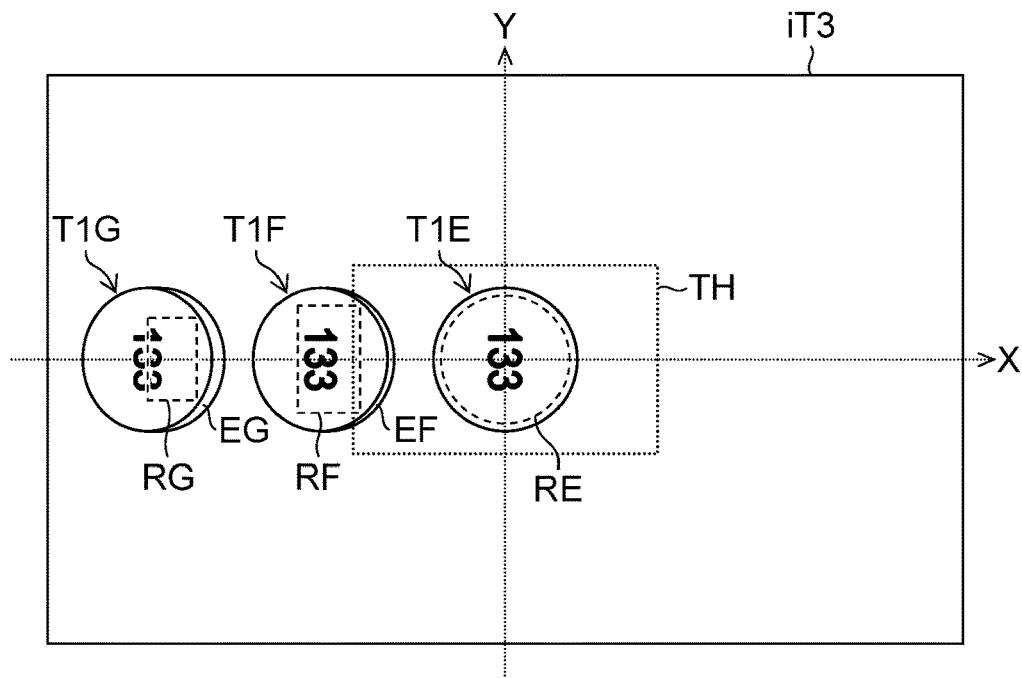
FIG. 12A is still another diagram showing setting of the region of interest according to the position of the medicine.
Figure 12B:
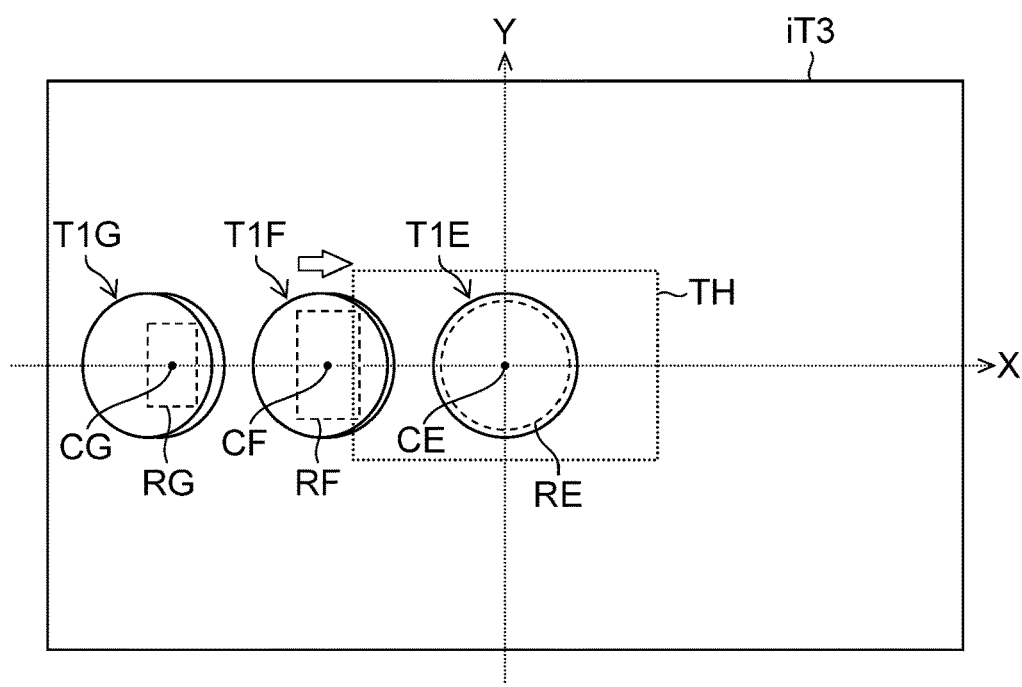
FIG. 12B is still another diagram showing setting of the region of interest according to the position of the medicine.

In the above, FIGS. 10A to 11B illustrate the case where the medicine is horizontally oriented (orientation of the engraved stamp is the X-axis direction). A case where the medicine is vertically oriented (orientation of the engraved stamp is along the Y-axis direction) will be described. FIGS. 12A and 12B are diagrams showing setting of region of interest in the case where the medicine is vertically oriented in the state shown in FIGS. 10A and 10B. In FIG. 12A, for a medicine T1E (medicine T1 exists at a center part of a captured image iT3), the processing unit 10 (region-of-interest setting unit 10D) sets a region of interest RE having a circular shape (shape similar to the medicine T1), similarly to FIGS. 10A and 10B. For a medicine T1F (medicine T1 exists at the intermediate part in the −X direction in the captured image iT3), the processing unit 10 (region-of-interest setting unit 10D) sets a region of interest RF having a rectangular shape (the region of interest RF is smaller in size than the region of interest RE) such that the region of interest RF does not include an area on the −X side of the medicine T1F (area strongly influenced by the light source 13 on the −X side) and a side surface area EF. For a medicine T1G (medicine T1 exists at the end part in the −X direction in the captured image iT3), a region of interest RG having a rectangular shape (the region of interest RG is smaller in size than the region of interest RF) is set such that the region of interest RG does not include the −X side of the medicine T1G and a side surface area EG.

FIG. 12B is a diagram showing positions of centers CE, CF and CG of the regions of interest RE, RF and RG, similarly to FIGS. 10B and 11B. The center CE is on a center of the medicine T1E, that is, a center of the captured image iT3. The centers CF and CG are moved to the center side (+X side) of the captured image iT3 (an amount of movement of the center CG> an amount of movement of the center CF). Here, illustration of the engraved stamps are omitted in FIG. 12B. Similarly to the above description about FIGS. 10A to 11B, the processing unit 10 (template generating unit 10E) sets the position, shape and size of the template according to the region of interest set in this way (step S158 in FIG. 8; template generating process).

Thus, it is preferable to set a region of interest based on an orientation of a medicine in addition to a position, and then, set a template according to the region of interest. The processing unit 10 (medicine detecting unit 10C) can detect the orientation of the medicine, for example, at step S140 (medicine detecting process).

In the flowchart of FIG. 8, when the setting of the region of interest (step S157) and the generation of the template (step S158) are finished, the flow returns to the flowchart of FIG. 6, and the processing unit 10 (collating unit 10F) collates the template with the region of interest to determine whether the audit-target medicine and the medicine shown by the master image are the same medicine or not (step S160; collating process). At the time of the collation, at least one of the region of interest and the template may be turned so that their orientations match each other. Further, at least one of the region of interest and the template may be magnified or reduced so that their sizes match each other. The processing unit 10 (collating unit 10F) outputs information indicating whether the audit-target medicine and the medicine shown by the master image are the same or not (to be described later).

When the collation for one audit-target medicine is finished, the processing unit 10 (collating unit 10F) determines at step S170 (collating process) whether collation between one medicine described in the prescription and images of all audit-target medicines has finished or not. If a positive determination result is obtained (step S170: YES), the flow proceeds to step S180. If a negative determination result is obtained (step S170: NO), the flow returns to step S130, where an image of the next audit-target medicine is obtained and collated (step S140; collating process).

At step S180, it is determined whether or not collations have finished for all medicines written in the prescription (all medicines to be packaged in each packaging bag TP). The processes of steps S120 to S170 are repeated for all the other medicines written in the prescription until a positive determination result is obtained. If the positive determination result is obtained (step S180: YES), the flow proceeds to step S190. At step S190, the processing unit 10 (collating unit 10F) determines whether the processes have been finished for all the packaging bags TP included in the medicine strip package PB or not, and repeats the processes of steps S110 to S180 (medicine detecting process, region of interest setting process, template generating process and collating process) until a positive determination result is obtained.

When the processes have been finished for all the packaging bags TP, the processing unit 10 (collating unit 10F and display controlling unit 10G) outputs the collation result (information indicating whether the audit-target medicines and medicines shown by master images are the same or not) (step S200; collating process). For example, as shown in FIG. 13, images of audit-target medicines which are determined to be the "medicine T1 (see FIGS. 7 and 9)" are displayed in a list on the monitor 32. Alternatively, it is possible to display an indication about "the audit-target medicine and the medicine shown by the master image are the same, similar or dissimilar" for each audit-target medicine and/or for each master image, or display a value of similarity. The processing unit 10 (collating unit 10F) may cause the collation result (collation result 20E) to be stored into the storing unit 20 (step S200; collating process).

As described above, according to the first embodiment, since it is possible to avoid or reduce distortion of a medicine shape, blur and inclusion of an end part into an image, and the like due to a position of an audit-target medicine, influence on collation accuracy by collation conditions can be reduced and robustness in collation accuracy can be improved.

An embodiment of the present invention and examples have been described above. The present invention is not limited to the aspects described above, and various modifications are possible within a range not departing from the spirit of the present invention.

REFERENCE SIGNS LIST 1 dispensing audit support apparatus
10 processing unit
10A prescription information inputting unit
10B imaging unit
10C medicine detecting unit
10D region-of-interest setting unit
10E template generating unit
10F collating unit
10G display controlling unit
10H communication unit
12 lighting unit
13 light source
15A camera
15B camera
16 prescription reader
20 storing unit
20A prescription information
20B master image
20C attribute information
20D medicine image
20E collation result
30 displaying unit
32 monitor
40 operating unit
50 conveyance mechanism
CA center
CB center
CC center
CD center
CE center
CF center
CG center
EB side surface area
EC side surface area
ED side surface area
EF side surface area
EG side surface area
F1 engraved stamp
F2 engraved stamp
F3 engraved stamp
L light
PA imaging optical axis
PB medicine strip package
RA region of interest
RB region of interest
RC region of interest
RD region of interest
RE region of interest
RF region of interest
RG region of interest
S100 to S200 steps of dispensing audit support method
T1 medicine
T1A medicine
T1B medicine
T1C medicine
T1D medicine
T1E medicine
T1F medicine
T1G medicine
TP packaging bag
iM1 master image
iM2 master image
iT1 captured image
iT2 captured image
iT3 captured image

What is claimed is:

1. A dispensing audit support apparatus comprising:
a non-transitory and tangible recording medium configured to store a master image showing a medicine;
a camera configured to image an audit-target medicine to obtain a captured image; and
a processor, wherein the processor performs:
detecting a position of the audit-target medicine in the captured image;
determining a distance between the detected position of the audit-target medicine and a center of the captured image;
setting a region of interest in the image of the audit-target medicine, wherein a position, shape and size of the region of interest are set based on the detected position of the audit-target medicine in the captured image of the audit-target medicine;
reading out the master image showing a medicine written in a prescription from the non-transitory and tangible recording medium and generating a template based on the read master image, wherein a position, shape and size of the template are set according to the set region of interest; and
collating the template with the region of interest and outputting information indicating whether the audit-target medicine and the medicine shown by the master image are the same or not,
wherein the processor sets the region of interest smaller as the distance between the detected position of the audit-target medicine and the center of the captured image is longer, and generates the template smaller as the set region of interest is smaller, and
wherein the processor sets the region of interest in the image of the audit-target medicine in such a manner that the region of interest in the image of the audit-target medicine is moved more in a direction to the center of the captured image as the distance between the detected position of the audit-target medicine and the center of the captured image is longer, and generates the template in such a manner that the template for the master image is moved more as an amount of movement of the region of interest is larger.

2. The dispensing audit support apparatus according to claim 1, wherein the processor further performs:
moving the position of the region of interest in the captured image based on a direction of illumination relative to the audit-target medicine, and
moving the position of the template for the master image according to the region of interest being moved.

3. The dispensing audit support apparatus according to claim 1, wherein the processor further performs:
setting the region of interest and the template to be in shapes similar to the audit-target medicine, when a distance between the position of the audit-target medicine and a center of the captured image is equal to or below a threshold, and setting the region of interest and the template to be in rectangular shapes, when the distance between the position of the audit-target medicine and the center of the captured image exceeds the threshold.

4. The dispensing audit support apparatus according to claim 1, wherein the processor further performs:
turning at least one of the region of interest and the template in such a manner that orientations of the region of interest and the template match each other, and performing the collation.

5. The dispensing audit support apparatus according to claim 1, wherein the processor further performs:
magnifying or reducing at least one of the region of interest and the template in such a manner that sizes of the region of interest and the template match each other, and performing the collation.

6. The dispensing audit support apparatus according to claim 1, wherein
each of the template and the region of interest includes an engraved stamp area showing an engraved stamp provided on the medicine.

7. The dispensing audit support apparatus according to claim 1, wherein
the master image is an image based on an image obtained by imaging the audit-target medicine with the camera under lighting which is used when the collation is performed.

8. A dispensing audit support method by a dispensing audit support apparatus including a master image non-transitory and tangible recording medium configured to store a master image showing a medicine, and a camera configured to image an audit-target medicine to obtain a captured image, the method comprising:
a medicine detecting process of detecting a position of the audit-target medicine in the captured image, by the dispensing audit support apparatus;
a distance determining process of determining a distance between the detected position of the audit-target medicine and a center of the captured image;
a region of interest setting process of setting a region of interest in the image of the audit-target medicine, wherein a position, shape and size of the region of interest are set based on the detected position of the audit-target medicine in the captured image of the audit-target medicine, by the dispensing audit support apparatus;
a template generating process of reading the master image showing a medicine written in a prescription from the master image non-transitory and tangible recording medium and generating a template according to the region of interest based on the read master image, by the dispensing audit support apparatus; and
a collating process of collating the template with the region of interest and outputting information indicating whether the medicine shown by the captured image and the medicine shown by the master image are the same or not, by the dispensing audit support apparatus,
wherein the region of interest is set smaller as the distance between the detected position of the audit-target medicine and the center of the captured image is longer, and the template is generated smaller as the set region of interest is smaller, and
wherein the region of interest in the image of the audit-target medicine is set in such a manner that the region of interest in the image of the audit-target medicine is moved more in a direction to the center of the captured image as the distance between the detected position of the audit-target medicine and the center of the captured image is longer, and the template is generated in such a manner that the template for the master image is moved more as an amount of movement of the region of interest is larger.

* * * * *